United States Patent [19]

Neri et al.

[11] 4,064,146
[45] Dec. 20, 1977

[54] PROCESS FOR THE PREPARATION OF ALPHA-SUBSTITUTED EPOXIDE COMPOUNDS

[75] Inventors: Carlo Neri; Emilio Perrotti, both of San Donato Milanese, Italy

[73] Assignee: Snam Progetti S.p.A., Milan, Italy

[21] Appl. No.: 616,630

[22] Filed: Sept. 25, 1975

Related U.S. Application Data

[63] Continuation of Ser. No. 407,721, Oct. 18, 1973, abandoned, which is a continuation of Ser. No. 252,761, May 12, 1972, abandoned.

[30] Foreign Application Priority Data

May 13, 1971 Italy .................................... 24499/71

[51] Int. Cl.$^2$ .......................................... C07D 301/22
[52] U.S. Cl. .................................................. 260/348.16
[58] Field of Search ................................... 260/348 R

[56] References Cited

U.S. PATENT DOCUMENTS

| 1,925,317 | 9/1933 | Fuchs | 260/593 R |
| 2,434,631 | 1/1948 | Winkler et al. | 260/593 R |

FOREIGN PATENT DOCUMENTS

| 2,044,875 | 3/1971 | Germany | 260/348.5 L |

OTHER PUBLICATIONS

Jour. Am. Chem. Soc., vol. 36, p. 533.

*Primary Examiner*—Norma S. Milestone
*Attorney, Agent, or Firm*—Morgan, Finnegan, Pine, Foley & Lee

[57] ABSTRACT

An alpha-substituted epoxide, represented by the formula:

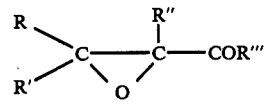

wherein R, R' and R''' are alkyl having up to 12 C atoms and R'' is hydrogen, is prepared by oxidizing, with molecular oxygen, the corresponding alcohol, represented by the formula:

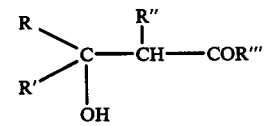

wherein R, R', R'' and R''' have the meaning given above, in the presence of a catalyst consisting of a monovalent copper complex.

6 Claims, No Drawings

PROCESS FOR THE PREPARATION OF ALPHA-SUBSTITUTED EPOXIDE COMPOUNDS

This is a continuation of application Ser. No. 407,721 filed Oct. 19, 1973, now abandoned, which, in turn, was a continuation of Ser. No. 252,761, filed May 12, 1972, and now abandoned.

The present invention relates to a process for the preparation of alpha-substituted epoxide compounds.

Particulary the present invention refers to an oxidation process, by molecular oxygen, of alcohols having a functional group in beta position with respect to the hydroxyl group, in the presence of catalysts based on copper compounds.

Processes for the preparation of substituted or unsubstituted epoxide compounds are known. They generally are based on mere stage reactions and employ difficultly available reagents, which remarkably influence the process economy.

However, nothing is known about the preparation of such epoxides by means of a metal catalyst.

We have found that it is possible to synthesize substituted epoxide compounds in a simple and cheap way, according to a method which is very interesting from an industrial point of view.

According to the present invention functional epoxide compounds are obtained which have the formula

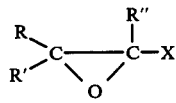

wherein R, R' and R" which may be the same or different, are hydrogen, hydrocarbon radicals having up to 12 C atoms, simple or substituted alkyl, cycloalyl or aryl radicals; X is a functional group selected from RCO—, —CN, —COOR, phenyl and substituted phenyl compounds, vinyl and the like, in which R has the aforesaid meanings.

Said compounds are obtained by oxidizing the corresponding beta-substituted alcohols: the oxidation is performed by molecular oxygen in the presence of copper compounds. The alcohols which are used have the following formula:

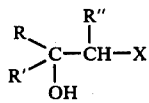

in which R, R', R" and X have the aforesaid meanings.

The reaction proceeds to the formation of the substituted epoxide according to the following scheme

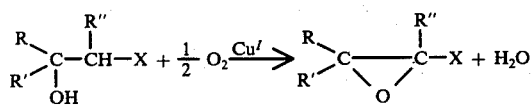

it being catalyzed by monovalent copper compounds.

Use may be made of the cuprous compounds in which copper is bound to an anion, such as CuX', wherein X' is a halide ion such as chloride, bromide, iodide or fluoride, or an anion selected from CN−, CH$_3$OCO−, enolate, nitrate, perchlorate and the like.

In order that a better solubility, and hence a higher reaction rate, may be obtained, an advantageous use may be made of monovalent copper complexes of the type CuX'L$_n$, wherein $n$ is an integer ranging between 1 and 6; X' has the aforesaid meaning; and L is a coordinating base, which may be simple or substituted, selected from phenanthrolines, dipyridils, pyridines, dimethylsulphoxide (DMSO), dimethylformamide (DMF), phosphines, arsines, stibines, imidazole, piperidine and so on. It is interesting to note that a behaviour similar to that of copper is shown by all metals having at least two valence states, and able to easily pass from one another, as, for instance, iron, manganese and cobalt.

A remarkably important aspect of the inventive process is the possibility of obtaining, at the end of the oxidation reaction, the starting monovalent copper compound, which can be again utilized so closing the catalytic cycle.

The oxidation process which we have invented can be simply carried out; it occurs with good yields and may be performed over a wide range of pressures and temperatures. It is possible to operate either in the presence or the absence of solvents or diluents. In the latter case the alcohol itself acts as reaction medium.

However, in the former case use can be made of solvents selected from simple or substituted aliphatic, aromatic and alicyclic hydrocarbons, ethers and some others, or from the afore mentioned bases.

In so far as the reaction temperatures are concerned, they can vary over a wide range and, as to the working pressure, the liquid phase is maintained.

Useful ranges are those from 15° to 150° C as to temperatures and from 1 to 30 atmospheres as to pressures.

If use is made of CuX'L$_n$, it is prepared according a known technique, and can be introduced as such into the reaction wessel, or it may be obtained by starting from Cu X' and L during the oxidation reaction itself.

Some other working particulars will be pointed out by the following illustrative example:

EXAMPLE — PREPARATION OF

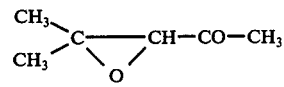

A mixture was prepared consisting of 48 g of diacetonealcohol and 3.5 g of pyridine; therein were dissolved 2 g of CuCl and the whole was subjected to an oxygen bubbling (2 l/hr) at 70° C.

After 12 hours, 2.5 g of CuClPy were separated by a filtration under nitrogen; the reaction products were analyzed in the solution by gas-chromatography. The conversion of diacetonalcohol was 28%, at a selectivity of 95% as epoxide and of 5% as acetone.

12.5 g of epoxide and 0.7 g of acetone were obtained.

What we claim is:

1. A process for the preparation of an alpha-substituted epoxide represented by the formula:

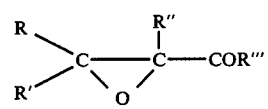

in which R, R' and R'" are alkyl having up to 12 C atoms and R" is hydrogen, wherein the corresponding alcohol represented by the formula

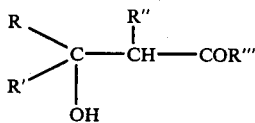

in which R, R', R" and R'" have the meanings given above, is oxidized with molecular oxygen in the presence of a catalyst represented by the formula: $CuXL_n$, in which X is a member of the group consisting of $Cl^-$, $Br^-$, $I^-$, $F^-$, $CN^-$, $CH_3OCO^-$, enolate, nitrate and perchlorate, $L_n$ is a coordinating base selected from the group consisting of: phenanthrolines, dipyridyls, pyridines, dimethylsulphoxide, dimethylformamide, phosphines, arsines, stibines, imidazole and piperidine, and $n$ is an integer in the range of from 1 to 6.

2. A process for the preparation of an alpha-substituted epoxide as claimed in claim 1, wherein the reaction is carried out in the presence of a solvent which is a member of the group consisting of aliphatic, aromatic and alicyclic hydrocarbons and ethers.

3. A process for the preparation of an alpha-substituted epoxide as claimed in claim 1, wherein the reaction is carried out at a temperature in the range between 15° and 150° C.

4. A process for the preparation of an alpha-substituted epoxide as claimed in claim 1, wherein the reaction is carried out at a pressure in the range between 1 and 30 atmospheres.

5. A process for the preparation of an alpha-substituted epoxide as claimed in claim 3 wherein R, R' and R'" are each methyl.

6. A process as claimed in claim 5 wherein X is $Cl^-$ and wherein $L_n$ is pyridine.

* * * * *